United States Patent [19]
Marchal et al.

[11] Patent Number: 5,879,913
[45] Date of Patent: Mar. 9, 1999

[54] PROCESS FOR THE PRODUCTION OF SOPHOROLIPIDS BY CYCLIC FERMENTATION WITH FEED OF FATTY ACID ESTERS OR OILS

[75] Inventors: Remy Marchal, Chatou; Michel Warzywoda, Rueil Malmaison; Bernard Chaussepied, La Celle Saint Cloud, all of France

[73] Assignee: Institut Francais du Petrole, France

[21] Appl. No.: 953,507

[22] Filed: Oct. 17, 1997

[30] Foreign Application Priority Data

Oct. 18, 1996 [FR] France .................................. 96 12797

[51] Int. Cl.⁶ ............................ C12P 19/00; C12P 19/62; C12P 7/64
[52] U.S. Cl. .............................. 435/75; 435/76; 435/100; 435/125; 435/134; 435/171; 435/225.4; 435/921
[58] Field of Search ................................ 435/75, 76, 100, 435/125, 134, 171, 255.4, 921

[56] References Cited

U.S. PATENT DOCUMENTS

| | | | |
|---|---|---|---|
| 5,616,479 | 4/1997 | Marchal et al. | 435/75 |
| 5,756,471 | 5/1998 | Hillion et al. | 514/25 |
| 5,767,255 | 6/1998 | Wullbrandt et al. | 435/255.4 |

FOREIGN PATENT DOCUMENTS

| | | |
|---|---|---|
| 2 670 798 | 6/1992 | France . |
| 2 692 593 | 12/1993 | France . |
| 254 959 | 3/1988 | German Dem. Rep. . |
| 252 002 | 12/1987 | Germany . |

OTHER PUBLICATIONS

Chemical Abstracts, vol. 122, No. 15 (Abstract No. 185450), 10 Apr. 1995.
Chemical Abstracts, vol. 119, No. 3 (Abstract No. 26744), 19 Jul. 1993.
ACS Caplus 1997:350747 127:120747 Abstract Fiehler et al "Fett/Lipid" (1997)99(1) 19–24.
ACS Caplus 1995:412062 122:185450 Abstract McCaffrey et al "J. Ferm. Bioeng." (1995) 79(2) 146–51.

*Primary Examiner*—Herbert J. Lilling
*Attorney, Agent, or Firm*—Millen, White, Zelano, & Branigan, P.C.

[57] ABSTRACT

A process for the production of sophorolipids by a stock of Candida bombicola or apicola in a medium that contains a source of nitrogen and a substrate is described. The process includes a first fermentation cycle that includes a stage of growth of the stock and a stage of production of a fermentation wort. The following stages are carried out at least once:

a) a portion of the wort is drawn off;

b) a mineral that contains nitrogen is added to the remaining portion to constitute a second medium;

c) a new fermentation cycle is carried out from this second medium, and another wort is produced.

Sophorolipids are recovered from these worts of stages (a) and (c). The duration of the first and new fermentation cycles is at least 30 hours.

18 Claims, No Drawings

PROCESS FOR THE PRODUCTION OF SOPHOROLIPIDS BY CYCLIC FERMENTATION WITH FEED OF FATTY ACID ESTERS OR OILS

This application is related to U.S. application Ser. No. 08/750,618 now U.S. Pat. No. 5,756,471 entitled Use of a Sophorolipid to Provide Free Radical Formation Inhibiting Activity, Elastase Inhibiting Activity, or Anti-inflammatory Activity filed Dec. 13, 1996.

The invention relates to a process for cyclic fermentation with feed of the substrate (cyclic fed batch culture) for the production of a composition of sophorolipids.

BACKGROUND

Sophorolipids are used in, for example, cosmetology, as antiradical-type agents and anti-elastic agents (WO 95/34282). They can also be used as co-surfactants in a process for clearing soil of pollution (EP-A 605 308).

It was mentioned in U.S. Pat. Nos. 3,205,150, 3,312,684 and EP-B 516803 that a quantity of sophorolipids was produced by a fermentation process that employed a Candida bombicola culture.

Sophorolipids are considered to be a mixture of compounds represented by formulas (1) and (2), in which $R^1$ represents hydrogen or the acetyl group and $R^2$ represents hydrogen or an alkyl group that contains 1 to 9 carbon atoms, or else $R^2$ represents hydrogen or a methyl group, when $R^3$ is an unsaturated chain that contains hydrocarbon with 13 or 17 carbon atoms.

These compounds can be used as cleaning agents and as emulsifiers, and they exhibit excellent hygroscopic properties and hydrophilic properties due to the sophorose portion of each of these molecules and hydrophobic properties that come from the fatty acid portions.

The preparation of sophorolipids is generally done in the presence of a substrate as described in U.S. Pat. No. 3,205,150. For example, this substrate can be made of hydrocarbons, saturated or unsaturated fatty acids, acid esters including glycerides, and vegetable oils such as soybean oil.

The substrate feed consists in ensuring, at intervals of about 12 to 24 hours, the discontinuous (batch) injection of a quantity of about 2% by weight relative to the initial reaction volume for each addition. The substrate feed is more advantageously carried out continuously (fed batch), as in the case of the European patent from applicant EP-B 516803.

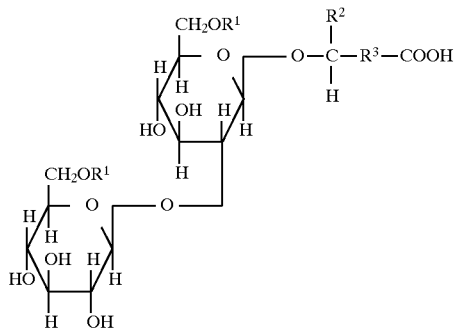

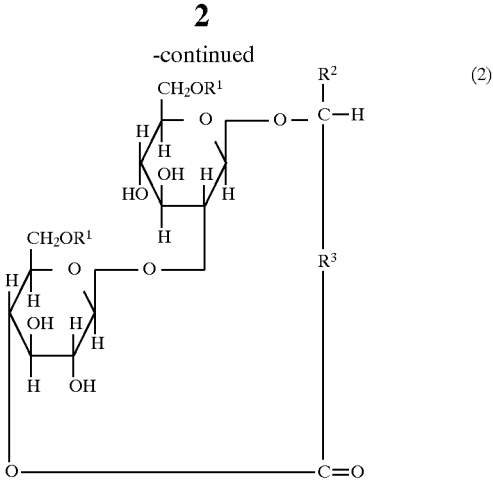

Structure of the sophorolipids:
(1): acid forms
(2): lactone forms

The discontinuous fermentation processes with the discontinuous (batch) feed of substrate or continuous (fed batch) feed of substrate have the classic drawbacks of discontinuous fermentation. Thus, the repeated use on an industrial scale of a series of discontinuous operations (by batch or by fed batch) means much down time in the operation of installations for cleaning and sterilization of the fermenter, which have to be repeated between each cultivation. Likewise, the propagation of the productive stock from its state of preservation in a gelose-treated tube, for example, to the production fermenter has to be done each time via an inoculation chain which involves the successive cultivation of the microorganism in fermenters of increasing sizes. This precultivation operation can take several days.

To avoid these drawbacks and constraints, technologists usually resort to continuous cultivation, in which the reactor is fed with culture medium and substrate at equivalent flow rates and the fermented wort is drawn off at an equivalent flow rate. The reaction volume is then constant. Routinely, continuous cultivation is carried out according to the chemostat method (Wang et al. 1979. Continuous Culture. In Fermentation and Enzyme Technology, John Wiley & Sons (eds), pp. 98–137). A nutrient for the culture medium is present in a limiting quantity, so that it is possible to monitor the steady-state concentration of the microorganism in the fermenter and to obtain stable operation of the system. When it is desired to produce metabolites (such as ethanol, for example), two or more fermenters that are arranged in series (bi-stage or multi-stage system) are generally used. In the first, the growth of the microorganism (first fermentation stage) is carried out with a medium that contains a limiting nutritive element (nitrogen, phosphorus), while the excretion of metabolites is carried out in the second reactor into which the fermentation wort from the first stage is admitted. Completely unexpectedly, it was observed that the stock that was placed under these production conditions progressively and quickly lost its excretion properties and that productivity was very inferior to that observed with fed batch.

Also studied, in Chem. Abstr., Vol. 122, No. 15, Apr. 10, 1995, No. 185450, was a fermentation process pertaining to the production of sophorolipids, so-called "self cycling fermentation (SCF)" during which, at the end of a period of time that corresponds to the growth period of the stock, half the fermentation wort obtained, which is replaced with fresh medium, is drawn off (see J. Ferment. Bio Eng. 1995, 79(2), p. 146, col. 1, 1.11 before the end, combined with the document Chem. Abstr.).

It is recommended that the cycle length after the growth period of the stock (doubling time) be extended by about 2 hours, so that each new cycle hardly exceeds 6 hours. With this approach, to be sure, the production capability of the stock is maintained, but the production of sophorolipids is very low, and it is very difficult to recover them short of extracting them with a solvent, which complicates the process and makes it even more expensive.

Other documents, such as Chem. Abstr., Vol. 119, No. 3, Jul. 19, 1993, No. 26744, Patent Applications FR-A.2 670 798 and FR-A. 2 692 593 describe a process for the production of sophorolipids by fed batch that includes a fermentation cycle.

Finally, Patent Applications DD-A-252 002 and DD-A-254 959 relate to cyclic fermentation processes for the production of proteins, steroids, and antibiotics by fungi and bacteria, whereby these processes neither describe nor suggest the production from yeast of glycolipids, which are products that are very different from those mentioned above.

SUMMARY OF THE INVENTION

An object of the invention is to remedy the drawbacks that are mentioned above. Another object of the invention is to improve the productivity of the system while obtaining the purest sophorolipids possible so as to avoid a stage for extraction by solvent of the products obtained. Another object is to increase the sophorolipid production time in fermentation tests that exceed the duration of discontinuous tests (by batch or fed batch), i.e., more than 180 hours, while ensuring high productivity levels.

A process for the preparation of sophorolipids that makes it possible to extend the production time and the volume productivity of sophorolipids was discovered. This process uses a special yeast cultivation technique, cyclic fermentation (Moser, A., 1985, Special Cultivation Techniques. In Biotechnology Vol. 2, Rehm, H. J. and Reed, G. (eds), pp. 311–347).

More specifically, the invention relates to a process for the production of a composition of sophorolipids that includes the cultivation in a reaction zone under aerated cultivation conditions of a yeast capable of producing a sophorolipid, preferably *Candida bombicola* or *Candida apicola* in a medium that contains a nitrogen source and a substrate. The process is characterized in that it includes a first fermentation cycle that includes a stage for growth of the stock and a stage for production of a fermentation wort that contains sophorolipids with a feed of the stock by substrate in the reaction zone. The process is also characterized in that the following stages are carried out at least once:

a) a portion of the fermentation wort is drawn off;

b) a mineral medium that contains nitrogen is added to the remaining portion of the wort to constitute a second medium;

c) a new fermentation cycle is carried out from this second medium, and another fermentation wort is produced.

The duration of said first and new fermentation cycles is at least 30 hours, e.g., about 30–130 hours. The sophorolipids are then recovered from the wort of stages (a) and (c).

It has been noted under these conditions that the productivity of the fermentation was improved while remarkable product purity was obtained, i.e., without the presence of a substantial quantity of fatty acids, e.g., <1%, so that subsequent fractionation to eliminate them was thus not required.

This advantage becomes more pronounced as the feed of the new fermentation cycles is carried out continuously.

A considerable gain in the inoculation chain has also been noted since it is possible to repeat the fermentation sequence (stages (a) to (c)) many times, for example, seven times without sophorolipid productivity being substantially affected.

The duration of each fermentation cycle will generally be at least 30 hours and preferably at least 70 hours, for example 80 to 130 hours, to make it possible, on the one hand, for the stock to increase sufficiently and, on the other hand, to allow enough sophorolipids for good decanting to accumulate.

According to an advantageous characteristic of the process, it is possible to separate, for example by decanting, the fermentation wort that is produced and to recover a fermentation wort which is freed of at least some of the sophorolipids and on which stages (a) to (c) can be carried out.

The purity of the products is then improved, i.e., the quantity of fatty acids that results from the hydrolysis of the substrate is such that subsequent fractionation to eliminate the fatty acids is not required.

According to another characteristic, after a portion of the wort has been drawn off, it is possible to replace this drawn-off portion of the wort with an approximately equal quantity of culture medium.

Advantageously, it is possible to draw off a quantity of wort such that at least 5% by weight remains, advantageously 15 to 45%, and preferably 20 to 40% of the wort in the reaction zone.

According to another characteristic of the process, it is possible to interrupt each fermentation cycle when the sophorolipid productivity during the so-called cycle decreases. It is preferably interrupted before 140 hours of fermentation and more particularly after a period of between 70 and 120 hours.

The last fermentation cycle, i.e., the fermentation, is generally halted when the productivity of sophorolipids that is calculated over the first 24 hours of production of this last cycle reaches 70% of the productivity of the first cycle that is calculated over the same production period.

According to a particularly advantageous characteristic that makes it possible to minimize the presence of fatty acids in the wort that is obtained, it is possible to keep the residual substrate concentration in the reaction zone during each fermentation cycle to a value that does not exceed 18 grams per liter of initial reaction volume while the reaction zone is fed with substrate.

By feeding the stock preferably approximately continuously at a rate of between 0.01 and 4 grams per hour and per liter of initial reaction volume, it is possible to monitor optimally this residual substrate concentration and to obtain the best results in terms of purity.

A discontinuous feed by small additions that are generally less than 10 g/l cannot be ruled out, however.

The substrate that is generally used is at least one animal oil, at least one vegetable oil and/or at least one ester of said oil, with said oil or said ester incorporating an aliphatic linear chain of 10 to 24 carbon atoms. Examples of useful oils are colza, sunflower, soya, and beef tallow.

With the stock *Candida bombicola* CBS 6009, excellent results in terms of growth and production of sophorolipids were obtained. The culture medium that is generally selected as well as the mineral medium that is supplied during stage (b) can contain sugar, for example, glucose.

The invention will be better understood based on the following examples:

EXAMPLE 1

(According to the Invention) Cyclic Cultivation with Continuous Feed and without Decanting of the Wort The stock *C. bombicola* CBS 6009 is used to inoculate a culture medium which, regardless of glucose, is lacking in substrate. The substrate is continuously added from the time cultivation begins. This is colza ethyl ester.

The composition of the culture medium that is used is as follows:

| | |
|---|---|
| Glucose | 100 g.l$^{-1}$ |
| (NH$_4$)$_2$SO$_4$ | 4 g.l$^{-1}$ |
| KH$_2$PO$_4$ | 1 g.l$^{-1}$ |
| MgSO$_4$, 7H$_2$O | 0.5 g.l$^{-1}$ |
| Dried corn maceration liquor | 5 g.l$^{-1}$ |

Glucose and MgSO$_4$, 7H$_2$O are sterilized in a 4-liter laboratory fermenter in solution in 1620 ml of water, while KH$_2$PO$_4$, (NH$_4$)$_2$SO$_4$ and dried corn maceration liquor are sterilized separately in an Erlenmeyer flask in solution in 180 ml of water. The sterilization of the two solutions is carried out in an autoclave at a temperature of 120° C. for 30 minutes, and the culture medium is reconstituted after the two solutions are cooled. It is primed with 200 ml of a preculture that is prepared in a Fernbach flask with the same medium as the fermentation medium but treated with 10 ml of colza ethyl ester. This flask is primed with approximately 1 g of a congelate of the *C. bombicola* stock. It is incubated while being stirred at a temperature of 25° C. After 24 hours, it provides the fermenter preculture.

Production fermentation is carried out in a four-liter fermenter on an initial reaction volume of two liters. The stirring of the medium is done with a RAYNERI turbine, whose speed of rotation is 1000 rpm. Aeration is set at 0.5 vvm of air under atmospheric pressure. After self-acidification of the medium of the culture, the pH is kept at a constant value of 3.5 with a 4N soda solution.

During fermentation, daily additions of glucose in solid form are carried out at a rate of 100 g at 24, 48, and 72 hours. The feeding of colza ethyl ester is carried out from the time that cultivation begins with a peristaltic pump whose feed rate is set at 2.1 g per hour. Sampling is used to monitor the production of sophorolipids, which are metered by the method of Göbbert et al. (Biotechnol. Lett. 1984, 6, 225–230). The production that begins after the growth phase increases with the addition of colza ethyl ester. After 96 hours of cultivation, a portion of the wort that is fermented is drawn off, leaving only one liter of wort in the fermenter. The latter is made up to two liters with one liter of fresh medium that contains glucose at a concentration of 100 g.l$^{-1}$. A second fermentation cycle with a duration of 96 hours is carried out with the same colza ester flow rate. The same operation of drawing off and making up as at the end of the preceding cycle is then carried out. Thus, overall, 7 fermentation cycles of 96 hours are carried out. 500 g of glucose is therefore provided to the culture in the first cycle and 400 g to each of the following cycles. The supply of colza ethyl ester is 201.6 g in each cycle.

The sophorolipids are recovered from different samplings that are taken at the end of each cycle, as well as in the final sampling, which consists of all the wort at the end of fermentation. In each sampling, the sophorolipids are allowed to decant for one hour, and they are recovered. They are suspended while being stirred with 1.5 liter of distilled water at a temperature of 45° C., and they are allowed to decant again for four hours. A second washing is carried out at 45° C. under conditions that are identical to those of the first washing. Thus, at the end of the second washing, a sample of hydrated sophorolipids is recovered on which the water content is measured by the Karl-Fisher method, the anhydrous sophorolipid content is measured by the method of Göbbert et al. (Biotechnol. Lett. 1984, 6, 225–230), and the fatty acid content is measured by the method of Davila et al. (Appl. Microbiol. Biotechnol. 1992, 38, 6–11). The fatty acids actually constitute the main impurity of the product. From these measurements are deduced the volume productivity levels relative to the initial volume (2 1) and the yields per unit of mass relative to the two carbon sources added, glucose and colza ethyl ester (Table 1).

TABLE 1

Performance Levels of Cyclic Fermentation with Continuous Ester Feed and Without Decanting of the Product

| Cycles | Sampling Times, Hours | Anhydrous Sophoro-lipids (g) | Fatty Acids in Sophoro-lipids (%) | Productivity Levels (g.l$^{-1}$ · h$^{-1}$) | Yields |
|---|---|---|---|---|---|
| 1 | 96 | 155 | 0.5 | 0.8 | 0.22 |
| 2 | 192 | 255 | 0.5 | 1.33 | 0.42 |
| 3 | 288 | 240 | <0.5 | 1.25 | 0.4 |
| 4 | 384 | 265 | 0.8 | 1.38 | 0.44 |
| 5 | 480 | 270 | 0.5 | 1.4 | 0.45 |
| 6 | 576 | 230 | <0.5 | 1.2 | 0.38 |
| 7 | 672 | 450 | 0.7 | 2.34 | 0.74 |
| Means | | 266 | 0.5 | 1.38 | 0.43 |

This example shows that the use of fermentation according to the invention makes it possible to maintain the production of sophorolipids for at least 672 hours of cultivation. The mean volume productivity over the duration of the test is 1.38 g.l$^{-1}$.h$^{-1}$, and the mean yield per unit of mass is 0.43. The performance levels of the first cycle are below the mean because the growth time of the stock is longer there; by contrast, those of the terminal cycle are higher because all of the wort that is contained in the fermenter is recovered.

EXAMPLE 2

(For Comparison): Fed or "Fed-Batch" Discontinuous Cultivation without Decanting of the Product In the same fermentation installation, the stock is cultivated according to the fed discontinuous cultivation method. The colza ester feed is kept constant at 2.1 g per hour. Daily additions of 100 g of glucose at 24, 48, 72, 96, 120, and 144 hours are performed. After 144 hours of cultivation, the assimilation speed of the glucose gradually slows down. Fermentation is halted after 192 hours, when the production of sophorolipids has stopped. The performance levels of this test are as follows (Table 2):

TABLE 2

Performance Levels of Fed (Fed-Batch) Discontinuous Fermentation

| Duration (hours) | Anhydrous Sophoro-lipids (g) | Fatty Acids in Sophoro-lipids (%) | Productivity Levels (g.l$^{-1}$ · h$^{-1}$) | Yields |
|---|---|---|---|---|
| 192 | 630 | 0.5 | 1.64 | 0.52 |

This example shows that the cultivation of the stock according to the fed or "fed-batch" discontinuous method does not make it possible to keep the excretion of sophorolipids from going beyond a cultivation duration that is approximately equal to 190 hours.

EXAMPLE 3

(For Comparison): Continuous Cultivation in Multi-Staged Chemostat

An installation of five fermenters that operate in series is used. The first has a useful volume of 0.44 liter, while the other four have a useful volume of two liters. The first is fed with colza ethyl ester at a rate of 2.1 g per hour. The stock is propagated in the first reactor for 24 hours (growth period), and then the multi-staged continuous cultivation is initiated by feeding the first reactor with a flow of fresh medium (with 100 g.l$^{-1}$ of glucose) of 44 ml.h$^{-1}$. At a temperature of 4° C. for periods of 96 hours, the wort that comes out of the last fermenter is recovered. The performance levels of the test in multi-staged chemostat are indicated in Table 3.

TABLE 3

Performance Levels of Continuous Cultivation in a Multi-Staged Chemostat

| Collection | Period (hours) | Anhydrous Sophorolipids (g) | Fatty Acids in Sophorolipidhorolipids (%) | Productivity Levels (g.l$^{-1}$ · h$^{-1}$) | Yields |
|---|---|---|---|---|---|
| 1 | 0 to 96 | 88 | 0.8 | 0.11 | 0.1 |
| 2 | 96 to 192 | 31 | 3 | 0.04 | 0.5 |
| 3 | 192 to 288 | 5 | 7.8 | 0.01 | 0.01 |
| 4 | 288 to 384 | <5 |  | <0.01 | <0.01 |
| 5 | 384 to 480 | <5 |  | <0.01 | <0.01 |
| 6 | 480 to 576 | <5 |  | <0.01 | <0.01 |
| 7 | 576 to 672 | <5 |  | <0.01 | <0.01 |

This example shows that when the stock is cultivated continuously according to the chemostat method, the stock is kept in the culture medium but gradually loses its ability to excrete sophorolipids.

EXAMPLE 4

Cyclic Cultivation with Discontinuous Feed and Decanting of the Product

Example 1 is repeated, replacing the continuous addition of colza ester with specific additions of ester that are equal to 201.6 g at the beginning of each cycle. The performance levels test are summarized in Table 4.

TABLE 4

Performance Levels of Cyclic Fermentation with Discontinuous Ester Feed and without Decanting of the Product

| Cycles | Sampling Times, Hours | Anhydrous Sophorolipids (g) | Fatty Acids in Sophorolipids (%) | Productivity Levels (g.l$^{-1}$ · h$^{-1}$) | Yields |
|---|---|---|---|---|---|
| 1 | 96 | 70 | 2.5 | 0.36 | 0.1 |
| 2 | 192 | 220 | 2.9 | 1.14 | 0.36 |
| 3 | 288 | 185 | 2 | 0.96 | 0.3 |
| 4 | 384 | 215 | 3.1 | 1.19 | 0.35 |
| 5 | 480 | 195 | 2.9 | 1.01 | 0.32 |
| 6 | 576 | 185 | 3.5 | 0.96 | 0.3 |
| 7 | 672 | 475 | 3 | 2.47 | 0.78 |
| Means |  | 220 | 2.8 | 1.15 | 0.35 |

This example shows that cyclic cultivation with discontinuous feed of the colza ethyl ester produces more sophorolipids than by fed-batch but fewer sophorolipids than by cyclic cultivation with continuous feed and without decanting of the product. In addition, the sophorolipids recovered contain more impurities than in the case of cyclic cultivation with continuous colza ester feed.

EXAMPLE 5

(According to the Invention) Cyclic Cultivation with Continuous Feed and Decanting of Sophorolipids Example 1 is repeated, modifying each cycle in the following way:

Before the fermentation wort is recovered, it is allowed to decant for one to two minutes. All the decanted sophorolipids and a portion of the fermentation wort are recovered, leaving in the fermenter only one liter of wort that is freed of sophorolipids. The results of the test are summarized in Table 5.

TABLE 5

Performance Levels of Cyclic Fermentation with Continuous Ester Feed and with Decanting of the Product

| Cycles | Sampling Times, Hours | Anhydrous Sophorolipids (g) | Fatty Acids in Sophorolipids (%) | Productivity Levels (g.l$^{-1}$ · h$^{-1}$) | Yields |
|---|---|---|---|---|---|
| 1 | 96 | 235 | <0.5 | 1.22 | 0.33 |
| 2 | 192 | 380 | <0.5 | 1.98 | 0.63 |
| 3 | 288 | 345 | <0.5 | 1.79 | 0.57 |
| 4 | 384 | 360 | <0.5 | 1.87 | 0.59 |
| 5 | 480 | 330 | <0.5 | 1.71 | 0.54 |
| 6 | 576 | 355 | <0.5 | 1.85 | 0.59 |
| 7 | 672 | 540 | <0.5 | 2.81 | 0.89 |
| Means |  | 363 | <0.5 | 1.89 | 0.59 |

This example shows that, according to the invention, the use of decanting of the sophorolipids and their recovery at the end of each cycle makes it possible to obtain a product that is very little contaminated by fatty acids. The productivity and the yield of the fermentation that is carried out under these conditions are higher than in the case of cyclic cultivation with continuous feed without decanting of the product.

EXAMPLE 6

Cyclic Cultivation with Discontinuous Feed and Decanting of Sophorolipids

Example 4 is repeated, whereby, at the end of each cycle, decanting and the recovery of the sophorolipids produced are initiated. The results of the test are indicated in Table 6.

TABLE 6

Performance Levels of Cyclic Fermentation with Discontinuous Ester Feed and with Decanting of the Product

| Cycles | Sampling Times, Hours | Anhydrous Sophorolipids (g) | Fatty Acids in Sophorolipids (%) | Productivity Levels (g.l$^{-1}$ · h$^{-1}$) | Yields |
|---|---|---|---|---|---|
| 1 | 96 | 225 | 1 | 1.17 | 0.32 |
| 2 | 192 | 360 | 1.3 | 1.87 | 0.59 |
| 3 | 288 | 350 | 1.7 | 1.82 | 0.58 |
| 4 | 384 | 345 | 0.9 | 1.79 | 0.57 |
| 5 | 480 | 330 | 1.1 | 1.71 | 0.54 |

TABLE 6-continued

Performance Levels of Cyclic Fermentation with Discontinuous Ester Feed and with Decanting of the Product

| Cycles | Sampling Times, Hours | Anhydrous Sophorolipids (g) | Fatty Acids in Sophorolipids (%) | Productivity Levels (g.l$^{-1}$ · h$^{-1}$) | Yields |
|---|---|---|---|---|---|
| 6 | 576 | 345 | 1.3 | 1.79 | 0.57 |
| 7 | 672 | 515 | 2 | 2.68 | 0.85 |
| Means | | 352 | | 1.83 | 0.57 |

This example shows that the productivity and yield of cyclic fermentation with discontinuous feed and decanting of sophorolipids are high. The purity of the sophorolipids, however, is not as good; this will make it necessary to carry out successive extractions with solvent, under hot conditions preferably, to reach a purity level that is comparable to that of the product of Example 5.

The preceding examples can be repeated with similar success by substituting the generically or specifically described reactants and/or operating conditions of this invention for those used in the preceding examples.

The entire disclosure of all applications, patents and publications, cited above and below, and of corresponding French application 96/12.797, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. Process for the production of a composition of sophorolipids comprising: cultivating in a reaction zone under aerated cultivation conditions of a stock of Candida bombicola or Candida apicola in a culture medium that contains a source of nitrogen and a substrate, wherein the process comprises a first fermentation cycle that includes a stage of growth of the stock and a stage or production of a fermentation wort that contains sophorolipids with a feed of the stock by substrate, in the reaction zone, with the process also being characterized in that the following stages are carried out at least once:

a) a portion of the fermentation wort is drawn off;
   b) a culture medium that contains nitrogen is added to the remaining portion of the wort to constitute a second medium;
   c) a new fermentation cycle is carried out from this second medium, and another wort is produced; with the duration of the first and new fermentation cycles being at least 30 hours and with the process also being characterized in that the sophorolipids are recovered from the wort of stages (a) and (c).

2. Process according to claim 1, wherein the fermentation wort that is produced is separated, and a fermentation wort that is freed of at least a portion of sophorolipids, on which stages (a) to (c) are carried out, is recovered.

3. Process according to claim 1 wherein to the remaining portion of the wort is added culture medium in an amount that is approximately equal to the quantity removed.

4. Process according to claim 1 wherein a quantity of wort is drawn off such that there remains at least 5% by weight of wort in the reaction zone.

5. Process according to claim 1 wherein each fermentation cycle is interrupted when the sophorolipid productivity during said cycle decreases and more is interrupted before 140 hours of fermentation.

6. Process according to claim 1 wherein the last fermentation cycle is halted when the productivity of sophorolipids, calculated over the first 24 hours of production of this last cycle, reaches 70% of the productivity of the first cycle, calculated over the same production period.

7. Process according to claim 1 wherein during each fermentation cycle the residual concentration of substrate in the reaction zone is kept at a value that does not exceed 18 grams per liter of initial reaction volume while the reaction zone is fed with substrate.

8. Process according to claim 1, wherein the substrate that is generally used is at least one animal oil, at least one vegetable oil, at least one ester of said oil, or a combination thereof, with said oil or said ester incorporating an aliphatic linear chain of 10 to 24 carbon atoms.

9. Process according to claim 1 wherein the culture medium contain sugar.

10. Process according to claim 1 wherein the stock is Candida bombicola CBS 6009.

11. Process according to claim 1 wherein the stock is fed by substrate in an approximately continuous manner at a feed rate of between 0.01 and 4 g per hour and per liter of initial reaction volume.

12. Process according to claim 1, wherein each fermentation cycle is interrupted when the sophorolipid productivity during said cycle decreases and is interrupted before after a period of about 70 and 120 hours.

13. Process according to claim 1, wherein a quantity of wort is drawn off such that there remains about 20 to 40% by weight of wort in the reaction zone.

14. A process of claim 1, wherein the substrate is an ethyl ester of colza.

15. Process according to claim 1, wherein the duration of said first and new fermentation of cycle of c) is at least 70 hours.

16. Process according to claim 1, wherein the duration of said first and new fermentation of cycle of c) is about 30–130 hours.

17. Process according to claim 1, wherein the feed of said stock by said substrate is discontinuous.

18. Process according to claim 1, wherein sophorlipids are decanted at the end of each fermentation cycle.

* * * * *